April 29, 1952 E. J. GARDNER Plant Pat. 1,086
DOUBLE PINK LILAC PLANT
Filed Oct. 28, 1950
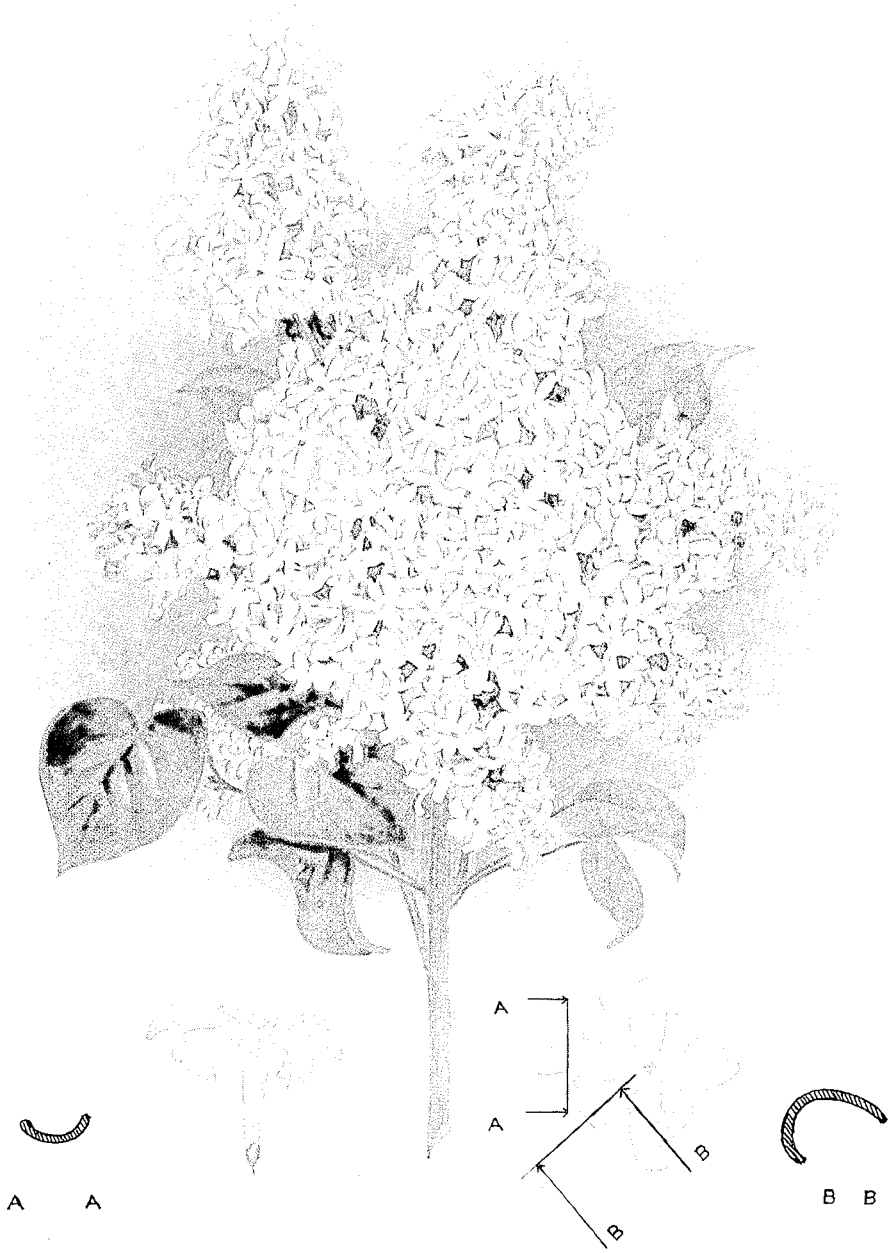
WITNESS
Addison J. Avery
INVENTOR
EDWARD J. GARDNER
Wheeler, Wheeler & Wheeler
ATTYS.

Patented Apr. 29, 1952

Plant Pat. 1,086

UNITED STATES PATENT OFFICE 1,086

DOUBLE PINK LILAC PLANT

Edward J. Gardner, Horicon, Wis.

Application October 28, 1950, Serial No. 192,755

1 Claim. (Cl. 47—60)

This invention pertains to a new variety of lilac (*Syringa vulgaris*) characterized by double pale pink blooms which more nearly approach a pure pink, when viewed in sunlight, than any lilac blooms previously known to me.

The accompanying illustration shows a panicle of bloom and associated leaves and a detail on an enlarged scale of a typical floret as it appears in plan and side elevation.

The original bush, from which I have reproduced other bushes asexually at Horicon, Wisconsin by rooting cuttings, and by grafting on *vulgaris* and other root stock, was a seedling of unknown ancestry. It was one of a large number of lilac plants raised from mixed seed of uncontrolled pollination which I collected from choice varieties in my nursery.

The habit of growth of the bush is extremely vigorous but not particularly distinctive, being similar to that of other lilacs. The foliage, however, is very slightly different from the foliage of lilac *vulgaris* or the varieties thereof commonly known as French hybrid lilacs. The terminal leaves on each stem have a distinct olive brownish cast, particularly in the veins, but this disappears and the leaves become uniformly green (Maerz and Paul, Dictionary of Color Plate 23–L–3) as they become older. The color and shape of the leaves and the shape of the florets and the form of the bloom clusters all suggest that one of the ancestors may have been a lilac *hyacinthiflora*. However, this possible parent is an early bloomer, whereas my improved lilac blooms with *vulgaris* and French hybrid lilacs, about mid-season.

The bloom panicles are large and loosely branching. The general color effect of the open flower is a uniform pale pink. The buds, however, have quite a deep mauve shade, that gradually lightens and disappears as the flower opens fully.

Individual florets resemble a hyacinch floret in form. They average about ⅞ inches across and are double. The calyx is minute as compared with the long, gamopetalons corolla, within which one or more additional carollae are nested. Each outer and inner corolla is substantially the same length as the outer and does not protrude therefrom, so that only one corolla is visible and the several layers of petals all appear to originate at nearly the same level. The petals of the top row, usually four in number, and spaced substantially uniformly at about 90°, are of different form from the others, being narrow and deeply channeled. There is sometimes a fifth narrow petal lying directly behind one of the others. Subdividing the angles between the petals of the top row are four broader petals, not appreciably channeled. Frequently there is a third row of petals corresponding in angular position with the narrow petals of the first row but broad and unchanneled, like those of the intermediate row. Only the petals of the lower row, whether it be the second or third row, spring from an external, visible corolla, and these lower petals are pronouncedly recurvant. The color of all petals, and the corolla is most nearly identified in Maerz and Paul Dictionary by Color Plate 1–E to F–(7). The fragrance is delicate but typical of lilacs.

Whereas most lilac blooms wither very shortly upon being picked and placed in water, the blooms of my improved lilac last unusually well and, when taken before aging on the bush, have maintained their color and form in water for several days without withering.

Having thus described some of the outstanding identifying characteristics of the lilac of my invention,

I claim:

The new and distinct variety of lilac plant as described and illustrated and characterized by its loose panicles of distinctive pale pink blooms, individual florets being double and having channeled narrow top petals and broad recurvant lower petals springing from immediately proximate levels.

EDWARD J. GARDNER.

No references cited.